(12) United States Patent
Braun

(10) Patent No.: US 10,806,170 B2
(45) Date of Patent: Oct. 20, 2020

(54) HEAT STERILIZED HIGH PROTEIN COMPOSITIONS COMPRISING WHEY PROTEIN AND AT LEAST ONE COMPONENT SELECTED FROM (I) A SACCHARIDE, (II) A PHOSPHATE AND (III) A CITRATE

(71) Applicant: NESTEC S.A., Vevey (CH)

(72) Inventor: Marcel Braun, Konolfingen (CH)

(73) Assignee: Societe des Produits Nestle S.A., Vevey (CH)

( * ) Notice: Subject to any disclaimer, the term of this patent is extended or adjusted under 35 U.S.C. 154(b) by 141 days.

(21) Appl. No.: 16/062,912

(22) PCT Filed: Nov. 22, 2016

(86) PCT No.: PCT/EP2016/078394
§ 371 (c)(1),
(2) Date: Jun. 15, 2018

(87) PCT Pub. No.: WO2017/102257
PCT Pub. Date: Jun. 22, 2017

(65) Prior Publication Data
US 2019/0000129 A1    Jan. 3, 2019

(30) Foreign Application Priority Data
Dec. 18, 2015  (EP) .................... 15201370

(51) Int. Cl.
*A23L 3/10*      (2006.01)
*A23L 33/19*     (2016.01)
(Continued)

(52) U.S. Cl.
CPC .............. *A23L 33/19* (2016.08); *A23J 3/08* (2013.01); *A23L 3/16* (2013.01); *A23L 33/125* (2016.08);
(Continued)

(58) Field of Classification Search
CPC ....................................................... A23L 3/10
See application file for complete search history.

(56) References Cited

U.S. PATENT DOCUMENTS

| | | | |
|---|---|---|---|
| 4,748,034 A | † | 5/1988 | De Rham |
| 2007/0048404 A1 | * | 3/2007 | Dias ........................ A23C 21/02 426/43 |

FOREIGN PATENT DOCUMENTS

| | | | |
|---|---|---|---|
| EP | 2 092 832 A1 | † | 8/2009 |
| WO | WO 2008/049939 A1 | † | 5/2008 |

(Continued)

OTHER PUBLICATIONS

Fundamentals of Dairy Chemistry, 3rd ed., N.P. Wong et al., Eds., Nan Nostrand Reinhold Company, New York, 1988.*
(Continued)

*Primary Examiner* — Rosanne Kosson
(74) *Attorney, Agent, or Firm* — K&L Gates LLP

(57) ABSTRACT

The present invention is directed to a heat sterilized composition comprising a protein source in an amount of 1 to 20% by weight of the composition, said protein source containing whey protein and at least one component selected from; (i) a saccharide component in an amount of 0.5 to 7.5% by weight of the composition, and/or (ii) a phosphate component in an amount of 0.03% to 3% by weight of the composition, and/or (iii) a citrate component in an amount of 0.07% to 5% by weight of the composition. The present invention is furthermore directed to a process for preparing a heat sterilized composition which comprises a protein source in an amount of 1 to 20% by weight based on the weight of the composition, said protein source containing whey protein, the process comprising at least the following steps: heating at a sterilisation temperature at a pH of 5.5 to 9.5 an aqueous solution of a protein source as defined herein. Finally, the invention concerns the use of whey protein and
(Continued)

Figure 1:
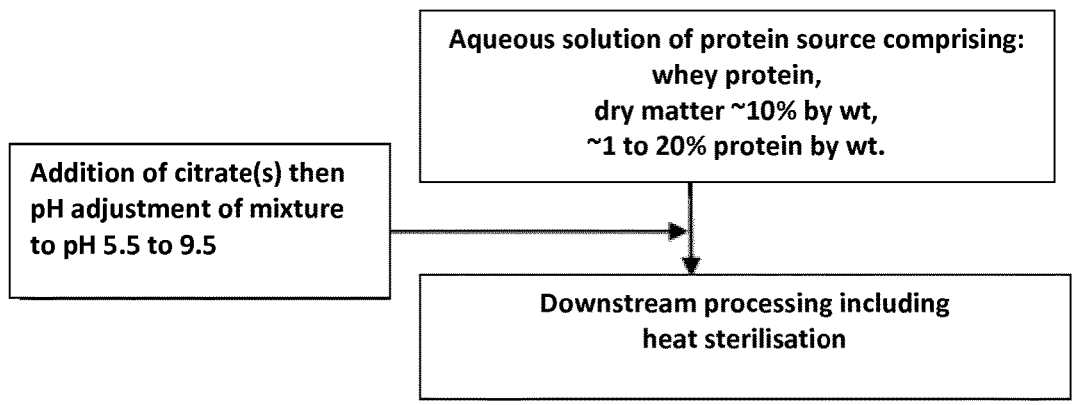

Protein Stabilization – with saccharide(s) addition along with citrate(s) and/or phosphate(s) in 0.5 to 7.5%, 0.07% to 5% and 0.03% to 3% by weight of the composition respectively.

at least one component as described for the heat sterilized composition, for preparing a heat sterilized composition and/or for controlling the viscosity of a liquid composition. The invention also concerns medical uses and treatments applying or using the inventive heat sterilized composition.

4 Claims, 7 Drawing Sheets

(51) Int. Cl.

| | | |
|---|---|---|
| A23J 3/08 | (2006.01) | |
| A23L 33/00 | (2016.01) | |
| A23L 33/18 | (2016.01) | |
| A23L 33/16 | (2016.01) | |
| A23L 33/125 | (2016.01) | |
| A23P 10/40 | (2016.01) | |
| A23L 3/16 | (2006.01) | |

(52) U.S. Cl.
CPC ............... *A23L 33/16* (2016.08); *A23L 33/18* (2016.08); *A23L 33/40* (2016.08); *A23P 10/40* (2016.08); *A23V 2002/00* (2013.01)

(56) References Cited

FOREIGN PATENT DOCUMENTS

| | | |
|---|---|---|
| WO | WO 2009/011573 A1 † | 1/2009 |
| WO | 2011112075 | 9/2011 |
| WO | 2012081971 | 6/2012 |
| WO | 2013129912 | 9/2013 |
| WO | 2015156662 | 10/2015 |

OTHER PUBLICATIONS

O. de Rham and S. Chanton, Role of Ionic Environment in Insolubilization of Whey Protein During Heat Treatment of Whey Products, pp. 939-949, 1984, Journal of Dairy Science vol. 67, No. 5.†

\* cited by examiner
† cited by third party

Protein Stabilization – with citrate(s) addition in 0.07% to 5% by weight of the composition Protein Stabilization – with citrate(s) and/or phosphate(s) addition in 0.07% to 5% and 0.03% to 3% by weight of the composition respectively Protein Stabilization – with saccharide(s) addition in 0.5 to 7.5% by weight of the composition Protein Stabilization – with saccharide(s) addition along with citrate(s) and/or phosphate(s) in 0.5 to 7.5%, 0.07% to 5% and 0.03% to 3% by weight of the composition respectively.

The addition of 2.6 g Na$_3$-citrate . 2H$_2$O per liter, strongly increase heat stability of whey protein isolate (Lacprodan DI 8790 10% solution).

The addition of 2.6 g Na$_3$-citrate . 2H$_2$O per liter, strongly increase heat stability of whey protein isolate (Lacprodan DI 8790 10% solution).

The addition of only 0.6 g NaH$_2$PO$_4$ · H$_2$O per liter, strongly increase heat stability of whey protein isolate (Bipro 10% solution).

The addition of only 0.6 g NaH$_2$PO$_4$ · H$_2$O per liter, strongly increase heat stability of whey protein isolate (Bipro 10% solution).

The addition of only 1.25 g $NaH_2PO_4 \cdot H_2O$ per liter, strongly increase heat stability of whey protein isolate (Lacprodan DI 8790 10% solution).

The addition of only 1.3 g $Na_3$-citrate $\cdot 2H_2O$ and 0.6 g $NaH_2PO_4 \cdot H_2O$ per liter, strongly increase heat stability of whey protein isolate (Bipro 10% solution).

Addition of a mixture of citrate and phosphate to Lacprodan DI 8790 strongly increase heat stability

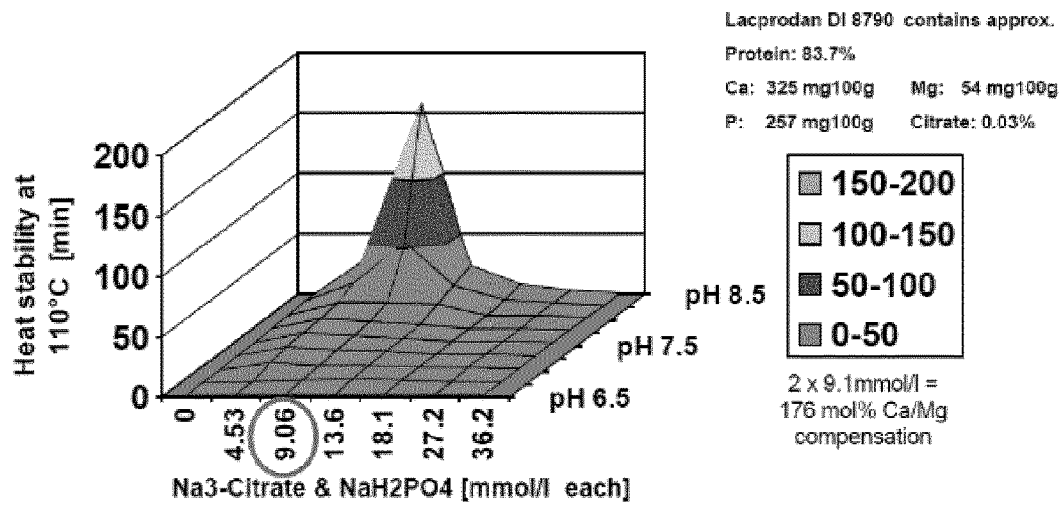

The addition of 2.6 g $Na_3$-citrate . $2H_2O$ and 1.25 g $NaH_2PO_4$ . $H_2O$ per liter, strongly increase heat stability of whey protein isolate (Lacprodan DI 8790 10% solution).

Figure 11

Addition of Sugars to Bipro strongly increase heat stability

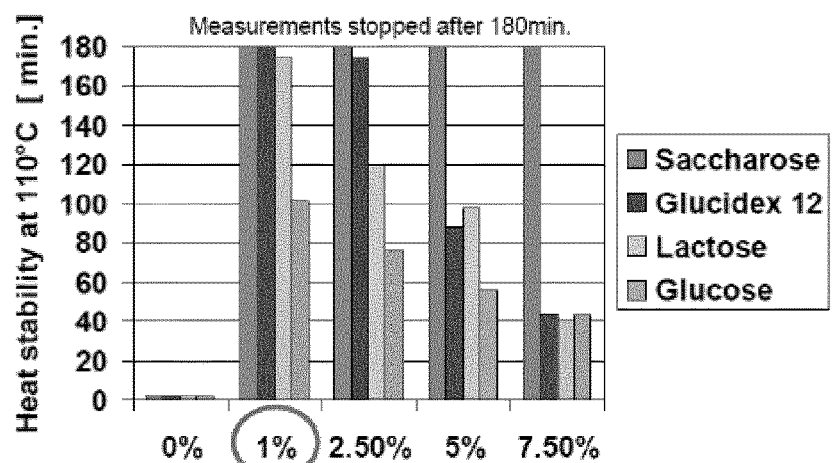

The addition of only 1% sucrose or maltodextrin (Glucidex 12) strongly increase heat stability of whey protein isolate (Bipro 10% solution, pH 7.5).

Figure 12

HEAT STERILIZED HIGH PROTEIN COMPOSITIONS COMPRISING WHEY PROTEIN AND AT LEAST ONE COMPONENT SELECTED FROM (I) A SACCHARIDE, (II) A PHOSPHATE AND (III) A CITRATE

CROSS REFERENCE TO RELATED APPLICATIONS

The present application is a National Stage of International Application No. PCT/EP2016/078394, filed on Nov. 22, 2016, which claims priority to European Patent Application No. 15201370.2, filed Dec. 18, 2015, the entire contents of which are being incorporated herein by reference.

FIELD OF THE INVENTION

The present invention is directed to a heat sterilized composition comprising a protein source in an amount of 1 to 20% by weight of the composition, said protein source containing whey protein and at least one component selected from; (i) a saccharide component in an amount of 0.5 to 7.5% by weight of the composition, and/or (ii) a phosphate component in an amount of 0.03% to 3% by weight of the composition, and/or (iii) a citrate component in an amount of 0.07% to 5% by weight of the composition.

The present invention is furthermore directed to a process for preparing a heat sterilized composition which comprises a protein source in an amount of 1 to 20% by weight based on the weight of the composition, said protein source containing whey protein, the process comprising at least the following steps: heating at a sterilisation temperature at a pH of 5.5 to 9.5 an aqueous solution of a protein source as defined herein.

Finally, the invention concerns the use of whey protein and at least one component as described for the heat sterilized composition, for preparing a heat sterilized composition and/or for controlling the viscosity of a liquid composition. The invention also concerns medical uses and treatments applying or using the inventive heat sterilized composition.

BACKGROUND

It is often advantageous to provide compositions containing a high protein content. This comes about since for instance an elderly person's ability to consume products may diminish. Alternatively, a sportsman or sportswoman whilst participating in sport may be in need of nutrition whilst the time taken to consume said nutrition should not impede their performance.

However, when increasing calories and/or the concentration of proteins in a nutritional liquid composition this increases the overall product viscosity and stability, and this has a disadvantageous effect on the palatability of the composition. In addition, minerals which may be incorporated or even bound to proteins can increase the mineral levels in a product with increased protein concentration to above acceptable nutritional limits. An increased viscosity can make the liquid nutritional composition difficult to consume or administer, and can also diminish the taste of the composition. Furthermore, the stability of such protein and energy dense liquid products may become a problem. This comes about since salt crystal formation during shelf life can become an issue, while it is desired that the nutritional product has a shelf life of at least 9 months, preferably at least 1 year.

One method to decrease the viscosity of a nutritional product containing protein is to hydrolyze the protein source therein, or employ a hydrolyzed protein source for the preparation thereof. However, such methods although allowing a reduced viscosity generally suffer the disadvantage that as a result of the hydrolysis a product with a bitter taste is provided.

Conventional protein hydrolysis processes are based on batch processes such as simple batch processes—including enzyme inactivation after hydrolysis time by product transfer to a heating unit. On an industrial scale batch processes often require a significant length of time, typically at least 1 to 3 hours. Furthermore, such processes allow little control regarding the degree of hydrolysis of the protein source and as a result provide products which are substantially bitter in taste. An example of such a batch process is for instance described in WO 2012/042013 A1.

In these processes many factors influence the process of hydrolysis, which makes these processes difficult to control and lead to a high risk that products are obtained have either high bitterness or are inadequate due to being too viscous.

Another method to decrease the viscosity of a nutritional product containing protein is to add for instance chelating agents such as phosphoric acid, citric acid or mixtures thereof. To this end WO 01/72135 A1 (Australian Food Industry Science Centre) and U.S. Pat. No. 6,455,082 B1 (Nestec) deal with the addition of phosphates to milk in order to stabilize the milk (containing casein micelles). Notably, they disclose an effect on viscosity for low protein systems e.g. 3 g per 100 mL.

EP 2 544 553 B1 (N.V. Nutricia) describes the use of phosphoric acid, citric acid or mixtures thereof for controlling the viscosity of an aqueous solutions of micellar casein comprising 6 to 20 g/100 mL. Notably, whey protein is not required. Furthermore, micellar casein suffers the disadvantage that one must carefully select the processing conditions since micellar casein is relatively unstable under different processing conditions, such as at high temperature and under acidic conditions.

EP 2 732 710 B1 (N.V. Nutricia) describes a liquid nutritional composition comprising 9 to tog protein per 100 mL of the composition, comprising phosphoric acid, citric acid or mixtures thereof. Notably said compositions may comprise whey protein in up to 15% by weight based on the total protein, although like EP 2 544 553 B1 a key requirement is the presence of micellar casein. In this light, EP 2 544 553 B1 contains substantial amounts of casein/casein micelles or combinations with polyphosphates.

Furthermore, the abovementioned prior art is silent with regard to the effect of adding a saccharide component on for instance the stability and viscosity of a high protein composition as described herein. In this light, none of the abovementioned prior art describes the specific combination of at least one component selected from (i) a saccharide component and (ii) a phosphate component. Also the specific combination of at least one component selected from (i) a saccharide component and (iii) citrate component is not described.

In view of the above, the problem underlying the present invention is therefore to provide compositions having a high protein content which are less bitter in taste or preferably are devoid of bitterness. Furthermore, such compositions should have a low viscosity. Finally, the present invention is confronted with the problem of providing a process allowing preparing such compositions.

DESCRIPTION OF THE INVENTION

The present inventors have surprisingly found that by employing a protein source comprising whey protein containing at least one component selected from (i) a saccharide component, and/or (ii) a phosphate component and/or (iii) a citrate component allows compositions to be prepared which are not bitter in taste. Furthermore, said compositions may have a high protein content of 1 to 20% by weight of the composition whilst at the same time having a low viscosity.

According to the present invention the underlying problem is therefore preferably solved by heat sterilized compositions as described in the independent claims and furthermore a process for preparing such heat sterilized compositions and uses according to independent claims as described herein. The dependent claims advantageously illustrate further preferred aspects of the inventive embodiments.

More preferably, the problem underlying the present invention is solved according to a first embodiment by a heat sterilized composition comprising a protein source in an amount of 1 to 20% by weight of the composition, said protein source containing whey protein and at least one component selected from (i) a saccharide component in an amount of 0.5 to 7.5% by weight of the composition, and/or (ii) a phosphate component in an amount of 0.03% to 3% by weight of the composition, and/or (iii) a citrate component in an amount of 0.07% to 5% by weight of the composition.

According to a preferred aspect the heat sterilized composition is a liquid composition, more preferably an aqueous composition. Such a liquid composition preferably has a viscosity of below 600 mPa s at 20° C./100 s$^{-1}$, most preferably of from 210 to 300 mPa s at 20° C./100 s$^{-1}$ or 250 to 400 mPa s at 20° C./100 s$^{-1}$ or 350 to 500 mPa s at 20° C./100 s$^{-1}$. Most preferably for said viscosity of below 600 mPa s at 20° C./100 s$^{-1}$ the protein source is in an amount of from 15 to 20% by weight of the composition, preferably 16 to 18% by weight of the composition.

In a specific aspect such a liquid composition preferably has a low viscosity, preferably a viscosity of below 400 or even below 200 mPa·s at 20° C./100 s$^{-1}$, typically with a lower range of at least 10 mPa s at 20° C./100 s$^{-1}$, preferably of from 10 to 195 mPa·s at 20° C./100 s$^{-1}$. Likewise such a liquid composition preferably has a low viscosity, preferably a viscosity of below 240 mPa s at 70° C./100 s$^{-1}$, most preferably of from 82 to 120 mPa s at 70° C./100 s$^{-1}$ or 98 to 156 mPa s at 70° C./100 s$^{-1}$ or 137 to 195 mPa s at 70° C./100 s$^{-1}$. Most preferably for said viscosity of below 240 mPa s at 70° C./100 s$^{-1}$ the protein source is in an amount of from 5 to 12% by weight of the composition, preferably in an amount of 8 to 10% weight of the composition.

In an further aspect such a liquid composition preferably has a low viscosity, preferably a viscosity of below 80 mPa s at 70° C./100 s$^{-1}$, preferably of from 4 to 78 mPa s at 70° C./100 s$^{-1}$.

The viscosity may be determined by methods known to a skilled person, e.g. by using a rotational viscosity meter using a cone/plate geometry, preferably by a Haake Reometer Haake RheoStress 100 5 n·cm, Thermo Scientific Germany—measurement setup: 0-600 s-1 (cr. Lin.); 300 seconds; 20° C. or 70° C. +/−0.1°; Data #300 Temperature controller Peltier TC80, measuring geometry: plate—plate 60 mm diameter 2 mm gap.

According to one further preferred aspect the heat sterilized composition may have a caloric density of at least 1.5 kcal/mL of the composition, preferably at least 1.8 kcal/mL, preferably at least 2.0 kcal/mL, preferably at least 2.2 kcal/mL of the composition, preferably wherein the caloric density is from 1 kcal/mL to 6 kcal/mL or 1.5 kcal/mL to 3.5 kcal/mL or 1.9 kcal/mL to 2.4 kcal/mL or 2.3 kcal/mL to 2.8 kcal/mL or from 2.6 kcal/mL to 3.2 kcal/mL.

In some aspects, the inventive heat sterilized composition may have a pH of 5.5 to 9.5, preferably a pH of 6.5 to 7.5 or a pH of 6.8 to 8 or a pH of 7.0 to 8.5 or a pH of 7.5 to 9 or a pH of 7.7 to 9.5.

According to a preferred aspect the inventive heat sterilized composition is an enteral composition or parenteral composition, most preferably an enteral composition.

Protein Source

According to the first defined embodiment the inventive heat sterilized composition comprises a protein source which contains whey protein.

The whey protein as contained in the inventive heat sterilized composition may be selected from e.g. whey protein isolate, acidified whey protein isolate, whey protein concentrate, whey powder, or further whey protein sources. Preferably the whey protein source is demineralised. Most preferably the whey protein in the inventive heat sterilized composition is whey protein isolate or whey protein concentrate.

In this light any commercially available whey protein isolates or concentrates may be used, i.e. whey protein obtained by any process for the preparation of whey protein known in the art, as well as whey protein fractions prepared there from or proteins such as [beta]-lactoglobulin (BLG), [alpha]-lactalbumin and serum albumin. In particular, sweet whey obtained as a by-product in cheese manufacture, acid whey obtained as a by-product in acid casein manufacture, native whey obtained by milk microfiltration or rennet whey obtained as a by-product in rennet casein manufacture may be used as the whey protein. The whey protein may be from a single source or from mixtures of any sources. Preferably the whey protein as contained in the inventive heat sterilized composition is native whey protein. Most preferably the whey protein as contained in the inventive heat sterilized composition is or comprises Bipro (available from e.g. Danisco—USA) or DWP 87 (e.g. Lacprodan DI8790 available from e.g. Arla foods—DK).

The whey proteins defined herein are not restricted to whey isolates from bovine origin, but pertains to whey isolates from all mammalian animal species, such as from sheep, goats, horses, and camels. Also, the inventive heat sterilized composition and also the inventive process according to the present invention applies to mineralised, demineralised or slightly mineralised whey preparations. By "slightly mineralised" is meant any whey preparation after elimination of free minerals which are dialyzable or diafiltrable, but which maintains minerals associated to it by natural mineralisation after preparation of the whey protein concentrate or isolate, for example. These "slightly mineralised" whey preparations have had no added mineral content.

The inventive heat sterilized composition may also comprise other heat sensitive proteins which may be selected from casein, egg protein, or from plant proteins such as pea protein, potato protein, soy protein, soy protein isolate or may be selected from combinations of any such protein sources and the like either alone or in combination. Said heat sensitive proteins are preferably native proteins.

In this light, the source of casein in the protein source may be selected from at least one of micellar casein, native casein, milk protein concentrate, milk protein isolate or milk powder; wherein if present the milk powder may be skimmed or full fat.

Generally, the inventive heat sterilized composition may also contain casein as a protein source. Nevertheless, according to one specific aspect the inventive heat sterilized composition does not contain casein. In case, however, casein is present casein is preferably present in combination with whey protein, preferably whey protein/casein in a weight ratio of 35/65 to 65/35, preferably 40/60 to 60/40, preferably 45/55 to 55/45. In a particularly preferred aspect, casein is present in a whey protein/casein weight ratio of 50/50.

Preferably the heat sterilized composition comprises less than 60% casein based on the protein source, preferably less than 50% casein based on the protein source or less than 40% casein based on the protein source.

Most preferably the heat sterilized composition comprises 5 to 60% by weight casein based on the protein source or 10 to 20% by weight or 15 to 30% by weight or 20 to 40% by weight or 25 to 50% by weight casein or 35 to 45% casein based on the protein source. In some aspects the protein source of the inventive heat sterilized composition may be obtained from the corresponding raw materials by processing and extraction techniques familiar to a person skilled in the art.

In this light, when the protein source of the inventive heat sterilized composition or components thereof comprises or contains a plant protein the plant protein may be obtained by e.g. an extraction process or a solvent extraction of corresponding protein containing plant parts, such as the dehulled and cracked soybeans, as it is known to a skilled person. In case of soy protein, for example, a soy protein isolate as a component of the protein source as defined herein may be obtained for instance by a process comprising:

1. optionally defattening of plant components by solvent extraction.
2. resolubilisation in water or mild alkali, separation of insolubles (fibres) and heat treatment of the extract.
3. separation of the oligosaccharides and phytic acid by acid precipitation and washing of the proteins.
4. optionally neutralisation and solubilisation of the precipitated soy proteins.

The thus obtained soy protein isolate can then be employed in the inventive heat sterilised composition as described herein.

According to the first defined embodiment the inventive heat sterilized composition contains a protein source in an amount of at least 1% by weight of the composition, preferably or protein source as defined herein.

More preferably, the protein source may be contained in an amount of at least 10% by weight of the composition, at least 12% by weight, at least 14% by weight or at least 16% by weight of the composition. According to a particularly preferred aspect the protein source is present in an amount of 1 to 20% by weight, more preferably 2 to 6% by weight or 3 to 7% by weight or 8 to 10% by weight or 11 to 20% by weight or 13 to 20 or 15 to 20% by weight of the composition, alternatively in an amount of from 1 to 14% by weight, or 15 to 20% by weight of the composition.

According to a preferred aspect the inventive heat sterilized composition contains whey protein in an amount of 1 to 20% by weight of the composition or 2 to 6% by weight or 3 to 7% by weight or 8 to 10% by weight or 9 to 12% by weight or 11 to 14% by weight or 13 to 16% by weight or 15 to 18% by weight of the composition. Most preferably 8 to 10% by weight.

According to a further preferred aspect the protein source may be present in the inventive heat sterilized composition in a protein concentration of up to 17 g/mL of the composition, preferably from 11 g/mL to 17 g/mL of the composition, preferably from 12 g/mL to 16 g/mL, preferably 13 g/mL to 15 g/mL of the composition.

Saccharide, Phosphate, Citrate

According to a preferred aspect, the at least one component contained in the inventive heat sterilized composition is or comprises (i) a saccharide component, which is preferably a monosaccharide, disaccharide, oligosaccharide or polysaccharide, which may be present alone or as mixtures.

Most preferably the inventive heat sterilized composition the at least one component is or comprises (i) a saccharide component which is a sugar, starch or cellulose.

According to a particularly preferred aspect the at least one component contained in the inventive heat sterilized composition is or comprises (i) a saccharide component which is a sugar selected from sucrose, maltodextrin, lactose or glucose, which may be present alone or as mixtures, most preferably sucrose or maltodextrin.

According to a preferred aspect the at least one component contained in the inventive heat sterilized composition is or comprises (i) a saccharide component, preferably in a total amount of 1% to 7.5% by weight. Most preferably the at least one component is (i) a saccharide component which is a sugar selected from sucrose or maltodextrin.

In another aspect of the heat sterilized inventive composition the at least one component is or comprises (ii) a phosphate component. Preferably the phosphate component is $NaH_2PO_4$, $K_2HPO_4$, $H_3PO_4$, $Na_2HPO_4$ and $H_4P_2O_7$ which may be present alone or as mixtures. Most preferably the inventive heat sterilized composition comprises (ii) a phosphate component which is $NaH_2PO_4$ or $KH_2PO_4$ which may be present alone or as mixtures. It may be advantageous when the inventive heat sterilized composition comprises (ii) a phosphate component which is $Na_2HPO_4$ or $K_2HPO_4$ which may be present alone or as mixtures.

In yet another aspect of the heat sterilized inventive composition the at least one component is or comprises (iii) a citrate component. Preferably the citrate component is or comprises trisodium citrate which may be present alone or as mixtures. Most preferably the inventive heat sterilized composition comprises (iii) a citrate component which is trisodium citrate.

In a further aspect of the inventive composition the at least one component is (i) a saccharide component and (ii) a phosphate component, preferably as defined above.

In a yet further aspect of the inventive composition the at least one component is (i) a saccharide component and (iii) a citrate component, preferably as defined above.

In one aspect of the inventive composition the at least one component is (ii) a phosphate component and (iii) a citrate component, preferably as defined above.

According to a particularly preferred aspect of the inventive composition the at least one component is (i) a saccharide component, (ii) a phosphate component and (iii) a citrate component, preferably as defined above. In said combination of components (i), (ii) and (iii) it was found to be particularly advantageous that the (i) saccharide is a sugar, preferably selected from sucrose, maltodextrin, lactose or glucose, most preferably sucrose and maltodextrin.

More preferably the inventive heat sterilized composition comprises (i) a saccharide component in an amount of 0.25 to 8.5% by weight of the composition, preferably 0.25 to 1% by weight of the composition or 0.5 to 1.5% by weight or 0.75 to 2% by weight or 1 to 2.5% by weight or 1.25 to 3% by weight or 1.5 to 3.5% by weight, or 1.75 to 4% by weight, or 2 to 4.5% by weight or 2.25 to 5% by weight or 2.5 to 5.5% by weight or 3 to 6% by weight or 3.5 to 7% by weight or 4.5 to 7.5% by weight of the composition. Most preferably the inventive heat sterilized composition comprises (i) a saccharide component in an amount of 0.5 to 1.5% by weight of the composition.

Likewise, more preferably the inventive heat sterilized composition comprises (ii) a phosphate component in an amount of 0.03 to 3% by weight or 0.03 to 0.5% by weight of the composition, preferably 0.06 to 0.125% by weight of the composition, or 0.08 to 0.16% by weight or 0.1 to 0.2% by weight or 0.15 to 0.3% by weight or 0.2 to 0.4% by weight or 0.3 to 0.5% or 1 to 2% by weight or 1.5 to 3% by weight of the composition. Most preferably the inventive heat sterilized composition comprises (ii) a phosphate component in an amount of 0.03 to 0.08% by weight of the composition or 0.11 to 0.13% by weight of the composition. Advantageously the inventive heat sterilized composition comprises (ii) a phosphate component in an amount of 0.6 to 1.25% by weight of the composition.

Preferably the inventive heat sterilized composition comprises (ii) a phosphate component in an amount of 88 mol % to 190 mol % Ca/Mg compensation or 4.5 to 9 mEq. $L^{-1}$.

Most preferably the inventive heat sterilized composition comprises (iii) a citrate component in an amount of 0.07 to 5% by weight of the composition, preferably 0.07 to 0.2 by weight or 0.13 to 0.26% by weight or 0.21 to 0.32% by weight or 0.28 to 0.38% by weight or 0.31 to 0.41% by weight or 0.35 to 0.5% by weight or 0.45 to 0.6% by weight or 0.55 to 0.7% by weight or 0.65 to 0.8% by weight or 0.75 to 0.9% by weight of the composition or 1 to 3% by weight or 2 to 4% by weight of the composition. Most preferably the inventive heat sterilized composition comprises (iii) a citrate component in an amount of 0.1 to 0.15% by weight of the composition or 0.2 to 0.3% by weight of the composition. Advantageously the inventive heat sterilized composition comprises (iii) a citrate component in an amount of 2 to 3% by weight, preferably 2.4 to 2.8% by weight of the composition. Preferably the inventive heat sterilized composition comprises iii) a citrate component in an amount of 88 mol % to 190 mol % Ca/Mg compensation or 4.5 to 9 mEq. $L^{-1}$.

Other Components

Following a further aspect the inventive heat sterilized composition also comprises micronutrients selected from vitamins, minerals and trace elements, which may be present either alone or in combination. Alternatively, in some aspects the inventive heat sterilized compositions may also not contain any micronutrients.

The term "micronutrient" as used herein refers to vitamins and (dietary) minerals that are required in the human diet in very small amounts.

The term "vitamin" as used herein, refers to any of various organic substances essential in minute quantities to the nutrition of most animals act especially as coenzymes and precursors of coenzymes in the regulation of metabolic processes. Vitamins have diverse bio-chemical functions, including function as hormones (for example, vitamin D), antioxidants (for example, vitamin C and vitamin E), and mediators of cell signalling, regulation of cell growth, tissue growth and differentiation (for example, vitamin A). The B complex vitamins, which is the largest in number, function as precursors for enzyme cofactor bio-molecules (co-enzymes) that help act as catalysts and substrates in metabolism. For instance Vitamin B6 and Vitamin B12. Other Vitamins, which may be present, include Vitamin K, Thiamin, Riboflavin, Niacin, Folic Acid, Biotin and Pantothenic Acid.

According to a particularly preferred aspect, the inventive heat sterilized composition comprises a mineral content of 1.5 to 5% by weight based on the protein source, preferably 1.5 to 2% by weight or 1.8 to 2.5% or 2.3 to 3% or 2.8 to 3.5% or 3.3 to 4% or 3.8 to 4.5% by weight based on the protein source, most preferably 1.6 to 2.2% by weight based on the protein source.

Minerals in this context are preferably dietary minerals such as e.g. calcium, magnesium, phosphorus, potassium, sodium, and sulphur. Preferably, calcium is contained in the inventive heat sterilized composition as a mineral and optionally at least one further dietary mineral as described before.

Further minerals that may be needed and employed in the inventive heat sterilized composition may be trace elements. Such trace elements are typically minerals that are needed in relatively small quantities, for example, chromium, cobalt, copper, chloride, fluorine, iodine, manganese, molybdenum, selenium, and zinc.

Accordingly, in some aspects, the inventive heat sterilized composition can include any combination of vitamins, minerals and trace elements that is useful in providing appropriate nutrition to the patient. The vitamins, minerals and trace elements may be used in the form of a mixture or formulation. The amounts of specific vitamins and minerals in the inventive heat sterilized composition may be determined by one of skill in the art.

The inventors have surprisingly found that low amounts of monovalent metal ions in the inventive heat sterilized composition may further enhance the low viscosity and stability of said composition as defined herein.

According to a preferred aspect the inventive heat sterilized composition comprises a total amount of monovalent metal ions selected typically from Na, K, more the sum of sodium and potassium (Na+K) in a low amount, preferably of up to 40 mg/g of the protein source, preferably less than 25 mg/g of the protein source, more preferably 0.01 to 40 mg/g of the protein source or 0.01 to 25 mg/g of the protein source, e.g. 0 to 5 mg/g of the protein source or 2 to 10 mg/g or 8 to 15 mg/g or 13 to 20 mg/g or 18 to 25 mg/g or 23 to 30 mg/g or 28 to 35 mg/g or 33 to 40 mg/g of the protein source. Advantageously the inventive heat sterilized composition comprises a total amount of monovalent metal ions selected typically from Na, K, more the sum of sodium and potassium (Na+K) in an amount of 7 to 9 mg/g of the protein source or 30 to 33 mg/g of the protein source.

In some aspects the amount of potassium in the inventive composition is typically up to 40 mg/g of the protein source, preferably less than 25 mg/g of the protein source, more preferably 0.01 to 40 mg/g of the protein source or 0.01 to 25 mg/g of the protein source, e.g. 0 to 5 mg/g of the protein source or 2 to 10 mg/g or 8 to 15 mg/g or 13 to 20 mg/g or 18 to 25 mg/g or 23 to 30 mg/g or 28 to 35 mg/g or 33 to 40 mg/g of the protein source. Advantageously the amount of potassium in the inventive composition is typically in an amount of 7 to 9 mg/g of the protein source or 18 to 24 mg/g of the protein source or 30 to 33 mg/g of the protein source.

In a further aspect, the amount of sodium in the inventive composition is typically up to 40 mg/g of the protein source, preferably less than 25 mg/g of the protein source, more preferably 0.01 to 40 mg/g of the protein source or 0.01 to 25 mg/g of the protein source, e.g. 0 to 5 mg/g of the protein source or 2 to 10 mg/g or 8 to 15 mg/g or 13 to 20 mg/g or 18 to 25 mg/g or 23 to 30 mg/g or 28 to 35 mg/g or 33 to 40 mg/g of the protein source. Advantageously the amount of sodium in the inventive composition is typically in an amount of 7 to 9 mg/g of the protein source or 8 to 14 mg/g of the protein source or 30 to 33 mg/g of the protein source.

The concentrations of monovalent metal ions in the above paragraphs are based on the total amount of protein in the protein source in the inventive composition, preferably on the total amount of whey protein as present in the inventive heat sterilized composition.

According to a further aspect, the inventive heat sterilized composition also may be provided as a food matrix. A food matrix is defined herein as being any type of food in liquid or powder form, e.g. a beverage, a food supplement, etc. wherein said food matrix contains the inventive heat sterilized composition as defined herein and optionally further proteins and/or fat and/or carbohydrate. Preferably, the inventive heat sterilized composition is liquid, more preferably provided as a beverage.

According to a particularly preferred aspect, the inventive heat sterilized composition is a nutritional composition, a nutritional supplement, an infant formula, an adult formula, a follow-up formula, a baby food formula, an infant cereal formula or a growing-up milk, an infant or child's food supplement, a children formula, an adult nutritional composition, maternal nutritional supplement, bariatric formula, elderly nutritional composition or health care formula; most preferably the aforesaid compositions are enteral compositions or parenteral compositions.

Furthermore, in some aspects the heat sterilized composition of the present invention may be in form of a supplement or may be used as a sole source of nutrition, e.g. be provided as a full meal. The term "supplement" as used herein refers to a nutrient that may be added to the diet or a meal thereof.

In the above context, an infant is defined herein as being up to 1 year of age, whereas children are defined as being at least from 1 to 7 years of age.

Furthermore, in this context, follow-up formulae are preferably designed to complement the changing diet of the older infant and provide a more balanced and complete food, better adapted to the child's nutritional needs at this age than normal milk. Growing-up milks (GUMs) can be considered a subgroup of follow-up formulas and are also included into the above-captioned definition. Such GUMs are adapted more particularly to the nutritional needs of children of one year or older, for example 1-6 years. Generally, GUMs are adapted specifically to the nutritional needs of children of a specific age. For example, there are GUMs for children of 1-3 years, 3-5 years and above 5 years old.

Finally, maternal nutrition is typically defined as being for pregnant and lactating women, and furthermore encompasses pre-conception administration to a woman willing to have a baby.

According to one preferred aspect the food matrix optionally may contain carbohydrate, probiotic, prebiotics, minerals, thickeners, buffers or agents for pH adjustment, chelating agents, colorants, emulsifiers, excipients, flavour agents, osmotic agents, preservatives, stabilizers, sugar, sweeteners, texturizers, and/or vitamins. For example, the nutritional compositions may contain emulsifiers and stabilizers such as soy lecithin, citric acid esters of mono- and di-glycerides, and the like. The optional ingredients can be added in any suitable amount.

According to a specific embodiment, the inventive heat sterilized composition may be used to prepare a food matrix as defined above, preferably a beverage, a food supplement, more preferably a nutritional composition, a nutritional supplement, an infant formula, an adult formula, a follow-up formula, a baby food formula, an infant cereal formula or a growing-up milk, an infant or child's food supplement, a children formula, an adult nutritional composition, maternal nutritional supplement, bariatric formula, elderly nutritional composition or health care formula;

In a further embodiment the inventive heat sterilized composition can also be used as a pharmaceutical and/or a nutraceutical product.

According to a further embodiment, uses of the inventive heat sterilized compositions as described herein, either as described initially or as obtained or obtainable according to the inventive process as described below, are contemplated. In one embodiment the inventive heat sterilized composition may be used for providing nutrition to a person in need thereof, wherein the person is preferably an elderly person, a person that is in a disease state, a person that is recovering from a disease state, a person that is malnourished, or a healthy person such as a sportsman or sportswoman or an active elderly. Within the context of the present invention, the nutritional ingredients of the heat sterilized composition, typically include proteins, fats and carbohydrates, which are selected depending on the product type.

According to a yet further embodiment the use of whey protein and at least one component is encompassed selected from (i) a saccharide component in an amount of 0.5 to 7.5% by weight of the composition and/or (ii) a phosphate component in an amount of 0.03% to 3% by weight of the composition and/or (iii) a citrate component in an amount of 0.07% to 5% by weight of the composition for preparing a composition comprising 1 to 20 weight % total protein, preferably a liquid composition, wherein preferably the liquid composition is an enteral composition or parenteral composition. More preferably a heat sterilized composition as defined herein.

In another embodiment of the present invention embodiment the use of whey protein and at least one component is provided selected from (i) a saccharide component in an amount of 0.5 to 7.5% by weight of the composition and/or (ii) a phosphate component in an amount of 0.03% to 3% by weight of the composition and/or (iii) a citrate component in an amount of 0.07% to 5% by weight of the composition, for controlling the viscosity of a liquid composition comprising 1 to 20 weight % total protein, wherein preferably the liquid composition is an enteral composition or parenteral composition. More preferably a heat sterilized composition as defined herein.

Preferably, the heat sterilized composition of the present invention as defined herein could be obtained by any process suitable for a skilled person. More preferably, the heat sterilized composition of the present invention could be obtained by a process as defined in further detailed below.

According to a further embodiment, the object underlying the present invention is therefore preferably also solved by a process for preparing a heat sterilized composition, preferably a heat sterilized composition as defined herein, preferably a heat sterilized enteral composition or heat sterilized parenteral composition, most preferably a heat sterilized enteral composition.

The present invention hence also describes a heat sterilized composition as described above, preferably a heat sterilized composition obtained or obtainable according to a process for preparing such a composition as defined herein. In this regard, said process may contain or comprise any of the amounts and ingredients as defined for the inventive heat sterilized composition.

Process

Hence, according to a particularly preferred embodiment the problem underlying the present invention is solved by a process for the preparation of a heat sterilized composition, more preferably a heat sterilized composition as described herein, which comprises a protein source in an amount of 1 to 20% by weight containing whey protein and at least one component selected from (i) a saccharide component in an amount of 0.5 to 7.5% by weight of the composition, and/or; (ii) a phosphate component in an amount of 0.03% to 3% by weight of the composition, and/or;

(iii) a citrate component in an amount of 0.07% to 5% by weight of the composition.

The process according to the invention typically includes the following steps:

heating at a sterilisation temperature at a pH of 5.5 to 9.5 an aqueous solution of a protein source which comprises whey protein and at least one component selected from;

(i) a saccharide component in an amount of 0.5 to 7.5% by weight of the heat sterilized composition, and/or;

(ii) a phosphate component in an amount of 0.03% to 3% by weight of the heat sterilized composition, and/or;

(iii) a citrate component in an amount of 0.07% to 5% by weight of the heat sterilized composition.

In one preferred aspect of the inventive process the protein source comprising whey protein and the at least one component are mixed, followed by a pH adjustment to pH 5.5 to 9.5, followed by heating at a sterilisation temperature. Preferably the inventive process employs a pH adjustment of a pH of 6.5 to 7.5 or a pH of 6.8 to 8 or a pH of 7.0 to 8.5 or a pH of 7.5 to 9 or a pH of 7.7 to 9.5. Most preferably the pH employed is a pH of 6.5 to 7.5 or a pH of 6.8 to 7.2, although it may be particularly advantageous to employ a pH of 6.5 to 7.5.

Most preferably the at least one component and the aqueous solution of a protein source which comprises whey protein are first mixed at 40 to 70° C., advantageously at a pH of 6.5 to 7.5, or at a pH as described above. Said mixture may then optionally be heat treated at 80 to 100° C. for 20 seconds to 1 minute. Other components as defined herein below may then be added, e.g. fat, minerals, trace elements, carbohydrates minerals alone or in combination. The thus obtained mixture may then be homogenized and is heat treated at a sterilization temperature at a pH of 5.5 to 9.5. The final step of the inventive process may be aseptic filling or spray drying of the thus obtained heat sterilized composition.

Protein Source

According to the inventive process as described herein a protein source is employed which contains whey protein.

The whey protein as used in the inventive process may be selected from e.g. whey protein isolate, acidified whey protein isolate, whey protein concentrate, whey powder, or further whey protein sources. Preferably the whey protein source is demineralised. Most preferably the whey protein as provided in the inventive process is whey protein isolate or whey protein concentrate.

In this light any commercially available whey protein isolates or concentrates may be used, i.e. whey protein obtained by any process for the preparation of whey protein known in the art, as well as whey protein fractions prepared there from or proteins such as [beta]-lactoglobulin (BLG), [alpha]-lactalbumin and serum albumin. In particular, sweet whey obtained as a by-product in cheese manufacture, acid whey obtained as a by-product in acid casein manufacture, native whey obtained by milk microfiltration or rennet whey obtained as a by-product in rennet casein manufacture may be used as the whey protein. The whey protein may be from a single source or from mixtures of any sources. Preferably the whey protein as employed in the inventive process is native whey protein.

Most preferably the whey protein employed in the inventive process is or comprises Bipro (available from e.g. Danisco—USA) or DWP 87 (e.g. Lacprodan DI8790 available from e.g. Arla foods—DK).

The present invention is not restricted to whey isolates from bovine origin, but pertains to whey isolates from all mammalian animal species, such as from sheep, goats, horses, and camels. Also, the inventive process according to the present invention applies to mineralised, demineralised or slightly mineralised whey preparations. By "slightly mineralised" is meant any whey preparation after elimination of free minerals which are dialyzable or diafiltrable, but which maintains minerals associated to it by natural mineralisation after preparation of the whey protein concentrate or isolate, for example. These "slightly mineralised" whey preparations have had no specific mineral enrichment.

The inventive process may also employ other heat sensitive proteins in the protein source, which may be selected from casein, egg protein, or from plant proteins such as pea protein, potato protein, soy protein, soy protein isolate or may be selected from combinations of any such protein sources and the like either alone or in combination. Said heat sensitive proteins are preferably native proteins.

In this light, the source of casein in the protein source may be selected from at least one of micellar casein, native casein, milk protein concentrate, milk protein isolate or milk powder; wherein if present the milk powder may be skimmed or full fat.

Preferably the protein source contains or consists of native protein.

Generally, the inventive process may also provide casein as a protein source. Nevertheless, according to one specific aspect the inventive process does not apply casein. In case, however, casein is used casein is preferably present in combination with whey protein, preferably with whey protein/casein in a weight ratio of 35/65 to 65/35, preferably 40/60 to 60/40, preferably 45/55 to 55/45. In a particularly preferred aspect, casein is used in a whey protein/casein weight ratio of 50/50.

It may be advantageous that the inventive process comprises less than 60% casein based on the protein source, preferably less than 50% casein based on the protein source or less than 40% casein based on the protein source of the heat sterilized composition. Most preferably the inventive process comprises 5 to 60% by weight casein based on the protein source or 10 to 20% by weight or 15 to 30% by weight or 20 to 40% by weight or 25 to 50% by weight casein or 35 to 45% casein based on the protein source of the heat sterilized composition.

In some aspects the protein source provided in the inventive process may be obtained from the corresponding raw materials by processing and extraction techniques familiar to a person skilled in the art, e.g. as described above.

According to the above-defined inventive process a protein source is provided in an amount of at least 1% by weight of the heat sterilized composition. More preferably, the protein source may be provided in an amount of at least 10% by weight of the heat sterilized composition, at least 12% by weight, at least 14% by weight or at least 16% by weight of the heat sterilized composition. According to a particularly preferred aspect the protein source is provided in an amount of 1 to 20% by weight, preferably more preferably 2 to 6% by weight or 3 to 7% by weight or 8 to 10% by weight or 11 to 20% by weight or 13 to 20% by weight or 15 to 20% by weight of the heat sterilized composition, alternatively in an amount of from 1 to 14% by weight, or 15 to 20% by weight of the heat sterilized composition.

According to the above-defined inventive process a whey protein is preferably employed in an amount of 1 to 20% by weight of the heat sterilized composition or 2 to 6% by weight or 3 to 7% by weight or 8 to 10% by weight or 9 to 12% by weight or 11 to 14% by weight or 13 to 16% by weight or 15 to 18% by weight of the composition. Most preferably 8 to 10% by weight of the heat sterilized composition.

According to a further preferred aspect the protein source may be provided in the inventive process in a protein concentration of up to 17 g/mL of the heat sterilized composition, preferably from 11 g/mL to 17 g/mL of the composition, preferably from 12 g/mL to 16 g/mL, preferably 13 g/mL to 15 g/mL of the heat sterilized composition.

Saccharide, Phosphate, Citrate

According to a preferred aspect the at least one component employed in the inventive process is or comprises (i) a saccharide component, which is preferably a monosaccharide, disaccharide, oligosaccharide or polysaccharide, which may be present alone or as mixtures.

Most preferably, said at least one component is or comprises (i) a saccharide component which is a sugar, starch or cellulose.

According to a particularly preferred aspect the at least one component employed in the inventive process is or comprises (i) a saccharide component which is a sugar selected from sucrose, maltodextrin, lactose or glucose, which may be present alone or as mixtures, most preferably sucrose or maltodextrin.

According to a preferred aspect the at least one component employed in the inventive process is or comprises (i) a saccharide component, preferably in a total amount of 1% to 7.5% by weight of the heat sterilized composition.

Most preferably the at least one component employed is (i) a saccharide component which is a sugar selected from sucrose or maltodextrin.

In another aspect the at least one component employed in the inventive process is or comprises (ii) a phosphate component. Preferably the phosphate component is NaH$_2$PO$_4$, K$_2$HPO$_4$, H$_3$PO$_4$, Na$_2$HPO$_4$ and H$_4$P$_2$O$_7$ which may be present alone or as mixtures.

Most preferably the inventive process comprises (ii) a phosphate component which is NaH$_2$PO$_4$ or KH$_2$PO$_4$ which may be present alone or as mixtures. It may be advantageous when the inventive process comprises (ii) a phosphate component which is Na$_2$HPO$_4$ or K$_2$HPO$_4$ which may be present alone or as mixtures.

In yet another aspect the at least one component employed in the inventive process is or comprises (iii) a citrate component. Preferably the citrate component is or comprises trisodium citrate which may be present alone or as mixtures. Most preferably the inventive process employs (iii) a citrate component which is trisodium citrate.

In a further aspect of the inventive process the at least one component employed is (i) a saccharide component and (ii) a phosphate component, preferably as defined above. In a yet further aspect of the inventive process the at least one component employed is (i) a saccharide component and (iii) a citrate component, preferably as defined above.

In one aspect of the inventive process the at least one component employed is (ii) a phosphate component and (iii) a citrate component, preferably as defined above.

According to a particularly preferred aspect of the inventive process the at least one component is (i) a saccharide component, (ii) a phosphate component and (iii) a citrate component, preferably as defined above. In said combination of components (i), (ii) and (iii) it was found to be particularly advantageous that the (i) saccharide is a sugar, preferably selected from sucrose, maltodextrin, lactose or glucose, most preferably sucrose and maltodextrin.

Most preferably the inventive process employs (i) a saccharide component in an amount of 0.25 to 8.5% by weight of the heat sterilized composition, preferably 0.25 to 1% by weight of the heat sterilized composition or 0.5 to 1.5% by weight or 0.75 to 2% by weight or 1 to 2.5% by weight or 1.25 to 3% by weight or 1.5 to 3.5% by weight, or 1.75 to 4% by weight, or 2 to 4.5% by weight or 2.25 to 5% by weight or 2.5 to 5.5% by weight or 3 to 6% by weight or 3.5 to 7% by weight or 4.5 to 7.5% by weight of the heat sterilized composition. Most preferably the inventive process employs (i) a saccharide component in an amount of 0.5 to 1.5% by weight of the heat sterilized composition.

Preferably the inventive process employs (ii) a phosphate component in an amount of 0.06 to 0.125% by weight of the heat sterilized composition, preferably 0.03 to 3% by weight or 0.08 to 0.16% by weight or 0.1 to 0.2% by weight or 0.15 to 0.3% by weight or 0.2 to 0.4% by weight or 0.3 to 0.5% or 1 to 2% by weight or 1.5 to 3% by weight of the heat sterilized composition. Most preferably the inventive process employs (ii) a phosphate component in an amount of 0.03 to 0.08% by weight or 0.11 to 0.13% by weight of the heat sterilized composition.

Advantageously the inventive process uses (ii) a phosphate component in an amount of 0.6 to 1.25% by weight of the heat sterilized composition.

Preferably the inventive process employs (ii) a phosphate component in an amount of 88 mol % to 190 mol % Ca/Mg compensation or 4.5 to 9 mEq. L$^{-1}$.

Most preferably the inventive process comprises (iii) a citrate component in an amount of 0.07 to 5% by weight of the heat sterilized composition, preferably 0.07 to 0.2 by weight or 0.13 to 0.26% by weight or 0.21 to 0.32% by weight or 0.28 to 0.38% by weight or 0.31 to 0.41% by weight or 0.35 to 0.5% by weight or 0.45 to 0.6% by weight or 0.55 to 0.7% by weight or 0.65 to 0.8% by weight or 0.75 to 0.9% by weight or 1 to 3% by weight or 2 to 4% by weight of the heat sterilized composition. Most preferably the inventive process employs (iii) a citrate component in an amount of 0.1 to 0.15% by weight of the composition or 0.2 to 0.3% by weight of the heat sterilized composition.

Advantageously inventive process employs iii) a citrate component in an amount of 2 to 3% by weight, preferably 2.4 to 2.8% by weight of the heat sterilized composition.

Preferably the inventive process applies iii) a citrate component in an amount of 88 mol % to 190 mol % Ca/Mg compensation or 4.5 to 9 mEq. L$^{-1}$.

Other Components

Additionally, according to one other preferred aspect micronutrients may be added to the protein source of the inventive process. Such micronutrients may be selected from vitamins, minerals and trace elements which may be present either alone or in combination. Alternatively, the protein source as employed in the inventive process does not contain any micronutrients or micronutrients may not be added to the inventive process.

According to a particularly preferred aspect a mineral content may be added to the protein source of the inventive process of 1.5 to 5% by weight based on the protein source, preferably 1.5 to 2% by weight or 1.8 to 2.5% or 2.3 to 3% or 2.8 to 3.5% or 3.3 to 4% or 3.8 to 4.5% by weight based on the protein source, most preferably 1.6 to 2.2% by weight based on the protein source.

The amounts of specific vitamins and minerals to be employed in the inventive process may be determined by one of skill in the art. More preferably, such specific vitamins and minerals are as defined above for the inventive composition.

Further minerals that may be added to the protein source of the inventive process may be trace elements. Such trace elements may include, for example, chromium, cobalt, copper, chloride, fluorine, iodine, manganese, molybdenum, selenium, and zinc.

Accordingly, in some aspects, the inventive process can include any combination of vitamins, minerals and trace elements that is useful in providing appropriate nutrition to the patient. The vitamins, minerals and trace elements may be used in the form of a mixture or formulation.

The inventors have surprisingly found that low amounts of monovalent metal ions in the inventive process are particularly advantageous, since this further enhances the low viscosity and stability of the heat sterilized composition as obtained there from.

According to a preferred aspect the protein source comprising whey protein may be provided in the inventive process such that the heat sterilized composition obtainable thereby contains a total amount of monovalent metal ions selected typically from Na and K, more sodium and potassium (Na+K) in a low amount, preferably an amount up to 40 mg/g of the protein source, preferably less than 25 mg/g of the protein source, more preferably 0.01 to 40 mg/g of the protein source or 0.01 to 25 mg/g of the protein source, e.g. 0 to 5 mg/g of the protein source or 2 to 10 mg/g or 8 to 15 mg/g or 13 to 20 mg/g or 18 to 25 mg/g or 23 to 30 mg/g or 28 to 35 mg/g or 33 to 40 mg/g of the protein source.

Advantageously the protein source comprising whey protein may be provided in the inventive process such that the heat sterilized composition obtainable thereby contains a total amount of monovalent metal ions selected typically from Na and K, more sodium and potassium (Na+K) in an amount of 7 to 9 mg/g of the protein source or 30 to 33 mg/g of the protein source.

In some aspects the protein source comprising whey protein may be provided in the inventive process such that the heat sterilized composition contains potassium typically in up to 40 mg/g of the protein source, preferably less than 25 mg/g of the protein source, more preferably 0.01 to 40 mg/g of the protein source or 0.01 to 25 mg/g of the protein source, e.g. 0 to 5 mg/g of the protein source or 2 to 10 mg/g or 8 to 15 mg/g or 13 to 20 mg/g or 18 to 25 mg/g or 23 to 30 mg/g or 28 to 35 mg/g or 33 to 40 mg/g of the protein source.

Advantageously the protein source comprising whey protein may be provided in the inventive process such that the heat sterilized composition contains potassium in the inventive composition in an amount of 7 to 9 mg/g of the protein source or 18 to 24 mg/g of the protein source or 30 to 33 mg/g of the protein source.

In a further aspect aspects the protein source comprising whey protein may be provided in the inventive process such that the heat sterilized composition obtainable thereby contains sodium typically in up to 40 mg/g of the protein source, preferably less than 25 mg/g of the protein source, more preferably 0.01 to 40 mg/g of the protein source or 0.01 to 25 mg/g of the protein source, e.g. 0 to 5 mg/g of the protein source or 2 to 10 mg/g or 8 to 15 mg/g or 13 to 20 mg/g or 18 to 25 mg/g or 23 to 30 mg/g or 28 to 35 mg/g or 33 to 40 mg/g of the protein source.

Advantageously the protein source comprising whey protein may be provided in the inventive process such that the heat sterilized composition obtainable thereby contains sodium in an amount of 7 to 9 mg/g of the protein source or 8 to 14 mg/g of the protein source or 30 to 33 mg/g of the protein source.

The concentrations of monovalent metal ions in the above paragraphs are preferably based on the total amount of protein in the protein source in the inventive composition, preferably on the total amount of whey protein as present in the inventive heat sterilized composition.

In a further preferred aspect of the inventive process the heat sterilisation step is carried out with a plate heat exchanger, extruder or by steam injection.

Accordingly, in some aspects of the inventive process step the heat sterilisation step is carried out by UHT treatment, preferably at above 135° C., preferably at 136 to 160° C., preferably 140 to 148° C. or 145 to 152° C. or 148 to 155° C., typically for a time of 1 second to 2 minutes, preferably 1 second to 1 minute or for 1 second to 30 seconds or for 1 second to 20 seconds or for 1 second to 10 seconds.

According to a particularly preferred aspect of the inventive process heating at a sterilisation temperature is carried out via a UHT treatment step, preferably at above 135° C. for a time of 1 to 5 seconds.

In another aspect of the inventive process the heat sterilisation step is carried out at 100° C. to 145° C., preferably at no to 130° C.

According to a preferred aspect of the inventive process generally any acid or base may be used to adjust the pH prior to the heat sterilisation step, such as sodium or potassium carbonate, sodium or potassium hydrocarbonate or ammonium hydroxide. Preferably, a base such as KOH or NaOH is employed to adjust the pH, although other bases including NaOH may also be employed to adjust the pH of 5.5 to 9.5, e.g. a pH of 6.5 to 7.5 or a pH of 6.8 to 8 or a pH of 7.0 to 8.5 or a pH of 7.5 to 9 or a pH of 7.7 to 9.5. Most preferably the pH employed is a pH of 6.5 to 7.5 or a pH of 6.8 to 7.2.

Those skilled in the art will recognize other means suitable for adjusting the pH. Suitable acids include, e.g. citric acid, hydrochloric acid, malic acid or tartaric acid most preferably citric acid.

To this end, in the inventive process only additives are used which preferably do not increase the monovalent metal ion content above 40 mg/g of protein, most preferably not above 25 mg/g of protein for the reasons as described earlier. For example, the use of potassium citrate or potassium hydroxide for adjusting the pH, or the use of NaCl should preferably be limited or most preferably avoided.

In a further aspect of the inventive process following the heat sterilisation step a heat sterilized liquid composition is obtained as a product of the inventive process, the heat sterilized liquid composition preferably being defined as herein above, more preferably comprising a protein source in an amount of 8 to 20% by weight of the heat sterilized composition, said liquid composition typically having a viscosity of below 600 mPa s at 20° C./100 s$^{-1}$, or likewise of below 200 mPa s at 20° C./100 s$^{-1}$, typically with a lower range of at least 10 mPa s at 20° C./100 s$^{-1}$, wherein preferably said heat sterilized liquid composition is an enteral composition or parenteral composition. Most preferably for said viscosity of below 600 mPa s at 20° C./100 s$^{-1}$ the protein source is in an amount of from 15 to 20% by weight of the composition, preferably 16 to 18% by weight of the composition, wherein preferably said heat sterilized liquid composition is an enteral composition or parenteral composition. The viscosity may be determined by methods known to a skilled person, e.g. by using a rotational viscosity meter using a cone/plate geometry, preferably as described for the inventive composition.

In a yet further aspect of the inventive process following the heat sterilisation step a heat sterilized liquid composition is obtained as a product of the inventive process, the heat sterilized liquid composition preferably being defined as herein above, more preferably comprising a protein source in an amount of 1 to 20% by weight of the heat sterilized composition, said liquid composition typically having a viscosity of below 240 mPa s at 70° C./100 $s^{-1}$, or likewise of below 80 mPa s at 70° C./100 $s^{-1}$, wherein preferably said heat sterilized liquid composition is an enteral composition or parenteral composition. Most preferably for said viscosity of below 240 mPa s at 70° C./100 $s^{-1}$ the protein source is in an amount of from 5 to 12% by weight of the composition, preferably in an amount of 8 to 10% weight of the composition.

In some aspects of the inventive process following the heat sterilisation step the heat sterilized composition is in an optional step dried to form a powder, preferably by spray drying, freeze drying, by lyophylisation or fluid bed agglomeration.

According to a particularly preferred aspect of the inventive process, following the heat sterilization step, the heat sterilized composition is in an optional step cooled to preferably 0 to 10° C., more preferably 1 to 5° C., e.g. 0 to 15° C., preferably 2 to 5° C. or 4 to 8° C. or 6 to 11° C. or 9 to 14° C., most preferably about 4° C.

According to a preferred aspect the entire heat sterilized composition obtained the steps of the inventive process is shelf stable. In some aspects of the inventive process the shelf life is at least 9 months, preferably at least 1 year, which preferably commences after the heat sterilization step, preferably after the optional cooling step which may follow the heat sterilisation.

Furthermore, in some aspects, the entire heat sterilized compositions obtained following the steps of the inventive process are not substantially bitter in taste and the liquid compositions obtained have a relatively low viscosity, low osmolality which are not jellified and/or not flocculated.

In a further aspect the entire heat sterilized composition obtained following the steps of the inventive process have improved stability, preferably an extended shelf life.

According to a further embodiment, uses of the inventive compositions as described herein, either as described initially or as obtained or obtainable according to the inventive process, are contemplated. According to one embodiment the inventive composition is particularly suitable for the use in providing nutrition to a person that is in a disease state or a person that is recovering from a disease state or a person that is malnourished.

As used herein, the term "a disease" refers to any derangement or abnormality of function; a morbid physical or mental state. See Dorland's Illustrated Medical Dictionary, (W.B. Saunders Co. 27th ed. 1988).

In some aspects treatment of such diseases or malnourishment is preferably accomplished by administering a therapeutically effective amount of an heat sterilized composition as defined according to the present invention to a subject in need thereof. According to a particularly preferred aspect such a heat sterilized composition is to be administered once daily, preferably twice daily, more preferably three times daily, wherein during administration preferably at least one unit or dose for administration is provided, as defined herein. Upon administration, preferably the total amount of energy to be administered per day is as defined before. As used herein, the term "subject" refers to an animal. Preferably, the animal is a mammal. A subject also refers to for example, primates (e.g., humans), cows, sheep, goats, horses, dogs, cats, rabbits, rats, mice, fish, birds and the like. In some aspects the subject is a human.

The term "therapeutically effective amount" of a heat sterilized composition of the present invention refers to an amount of the compound of the present invention that will elicit the biological or medical response of a subject, or ameliorate symptoms, slow or delay disease progression, or prevent a disease, etc. In a further aspect such a "therapeutically effective amount" is a packaged dose or unit as obtained.

According to one embodiment the inventive heat sterilized compositions as described herein, either as described initially or as obtained or obtainable according to the inventive process, are preferably suitable for use in infants (children under the age of 1). In some aspects the inventive compositions are also suitable for use by adults and children.

According to one aspect the heat sterilized composition obtainable from the inventive process is a nutritional composition, a nutritional supplement, an infant formula, follow-on formula, a baby food formula, an infant cereal formula or a growing-up milk, infant or child's food supplement, a children formula, adult nutritional composition, maternal nutritional supplement, bariatric formula, elderly nutritional composition or health care formula. Most preferably the heat sterilized composition obtainable from the inventive process is an enteral compositions or parenteral composition.

In some aspects the heat sterilized composition obtainable from the inventive process is for use in providing nutrition to a person in need thereof, wherein the person is preferably an elderly person, a person that is in a disease state, a person that is recovering from a disease state, a person that is malnourished, or a healthy person such as a sportsman or sportswoman or an active elderly.

Various embodiments of the invention have been described above. The descriptions are intended to be illustrative, not limitative. Thus, it will be apparent to one skilled in the art that certain modifications may be made to the invention as described without departing from the scope of the claims set out below.

For example, as described herein, "preferred embodiment" means "preferred embodiment of the present invention". Likewise, as described herein, "various embodiments" and "another embodiment" means "various embodiments of the present invention" and "another embodiment of the present invention", respectively.

Unless otherwise indicated, the term "at least" in the context of the present invention typically preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the present invention.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or sometimes when used herein with the term "having". When used herein "consisting of" excludes any element, step, or ingredient not specified in the claim element. When used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms.

Furthermore, percentages as described in the present invention can be interchangeably either % weight-by-weight (w/w) or % weight-by-volume (w/v), if not specifically indicated otherwise.

Finally, all publications and patents cited in this disclosure are incorporated by reference in their entirety. To the extent the material incorporated by reference contradicts or is inconsistent with this specification, the specification will supersede any such material.

Figures:

The following Figures are intended to illustrate the invention further. They are not intended to limit the subject matter of the invention thereto.

FIG. 1: Shows a schematic for the inventive process as described herein with citrate addition in 0.07% to 5% by weight of the heat sterilized composition. As one can see, the inventive process comprises the steps of adding to an aqueous solution of a protein source comprising whey protein (containing 1 to 20% by weight protein) the citrate component(s), mixing, then pH adjustment of the resulting mixture to pH 5.5 to 9.5. Said mixture is then heat treated such that a heat sterilised composition is provided comprising a protein source in 1 to 20% by weight based on the weight of the heat sterilized composition.

Figure 2:
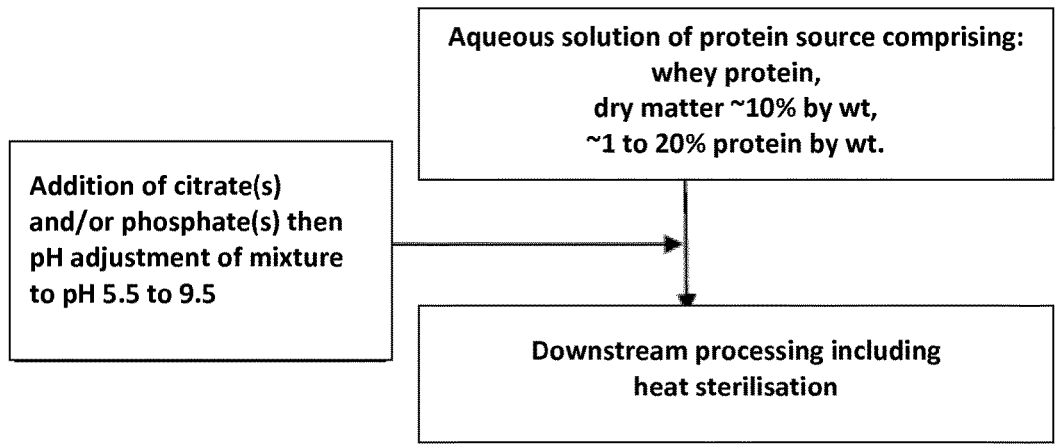

FIG. 2: Shows a schematic for the process as described herein with citrate and/or phosphate addition in 0.07% to 5% by weight of the heat sterilized composition and 0.03% to 3% by weight of the composition respectively. As one can see, the inventive process comprises the steps of to an aqueous solution of a protein source comprising whey protein (containing 1 to 20% by weight protein) is added the citrate component(s) and/or phosphate component(s), mixing, then pH adjustment of the resulting mixture to pH 5.5 to 9.5. Said mixture is then heat treated such that a heat sterilised composition is provided comprising a protein source in 1 to 20% by weight based on the weight of the heat sterilized composition.

Figure 3:
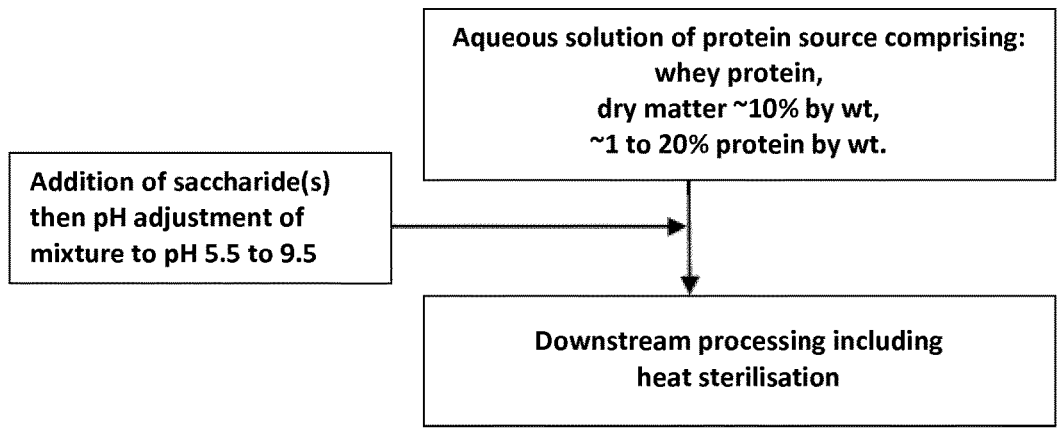

FIG. 3: Shows a schematic for the process as described herein with saccharide addition in 0.5 to 7.5% by weight of the heat sterilized composition. As one can see, the inventive process comprises the steps of adding to an aqueous solution of a protein source comprising whey protein (containing 1 to 20% by weight protein) the saccharide component(s), mixing, then pH adjustment of the resulting mixture to pH 5.5 to 9.5. Said mixture is then heat treated such that a heat sterilised composition is provided comprising a protein source in 1 to 20% by weight based on the weight of the heat sterilized composition.

Figure 4:
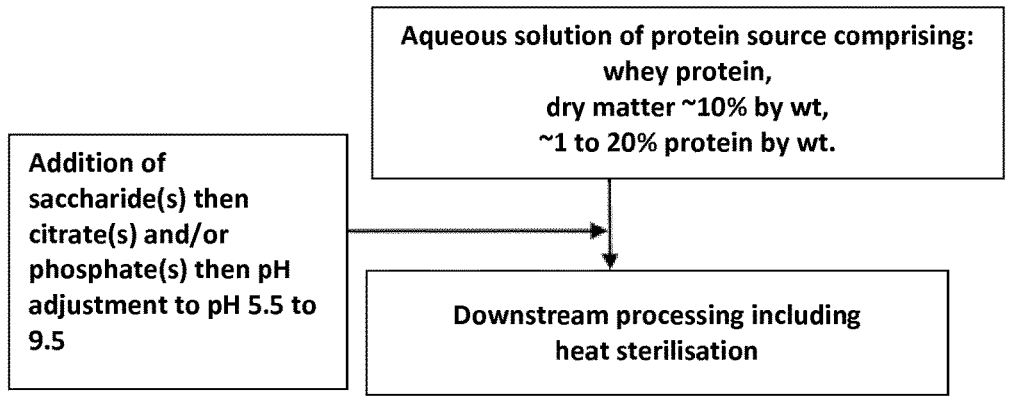

FIG. 4: Shows a schematic for the process as described herein with saccharide(s) addition along with citrate(s) and/or phosphate(s) in 0.5 to 7.5% by weight of the heat sterilized composition, 0.07% to 5% by weight of the heat sterilized composition and 0.03% to 3% by weight of the heat sterilized composition respectively. As one can see, the inventive process comprises the steps of to an aqueous solution of a protein source comprising whey protein (containing 1 to 20% by weight protein) is added the saccharide component(s), mixing, then adding the citrate component(s) and/or phopsphate component(s), mixing, then pH adjustment of the resulting mixture to pH 5.5 to 9.5. Said mixture is then heat treated such that a heat sterilised composition is provided comprising a protein source in 1 to 20% by weight based on the weight of the heat sterilized composition.

Figure 5:
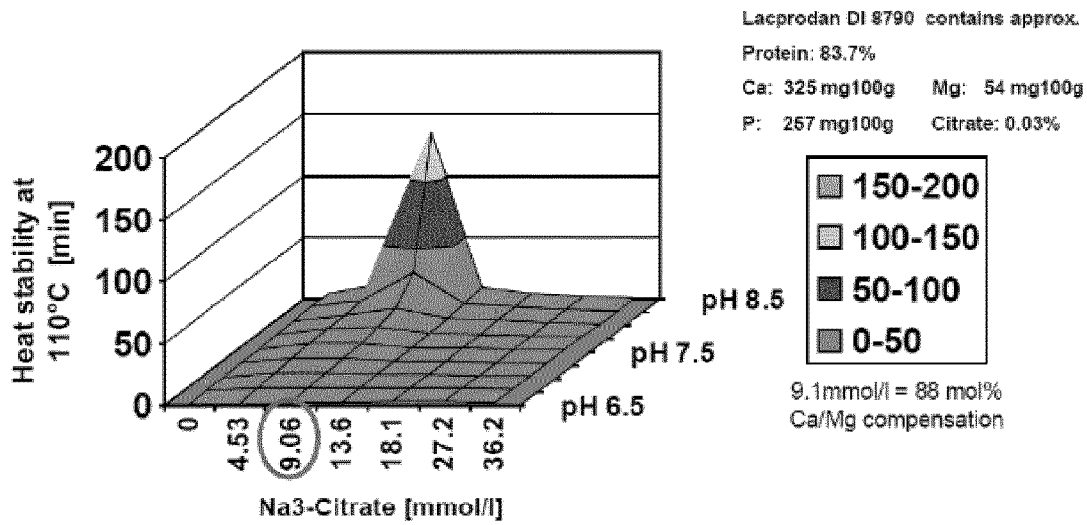

FIG. 5: Shows for the inventive composition as described herein that when the at least one component is citrate in 0.26% by weight of the heat sterilized composition (see example 1) a strong stabilization effect (see example 5 for protocol) is seen when the protein source is whey protein isolate, particularly at a pH of 8.5.

Figure 6:
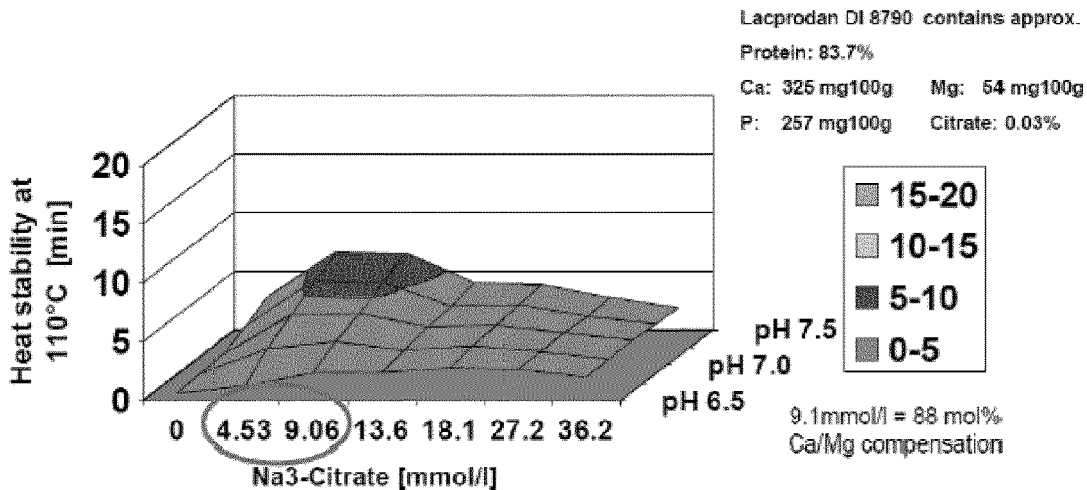

FIG. 6: Shows for the inventive composition as described herein that when the at least one component is citrate in 0.26% by weight of the heat sterilized composition (based on example 1) a slight but significant stabilizing effect with whey protein isolate is observed also at neutral pH values (see example 5 for protocol).

Figure 7:
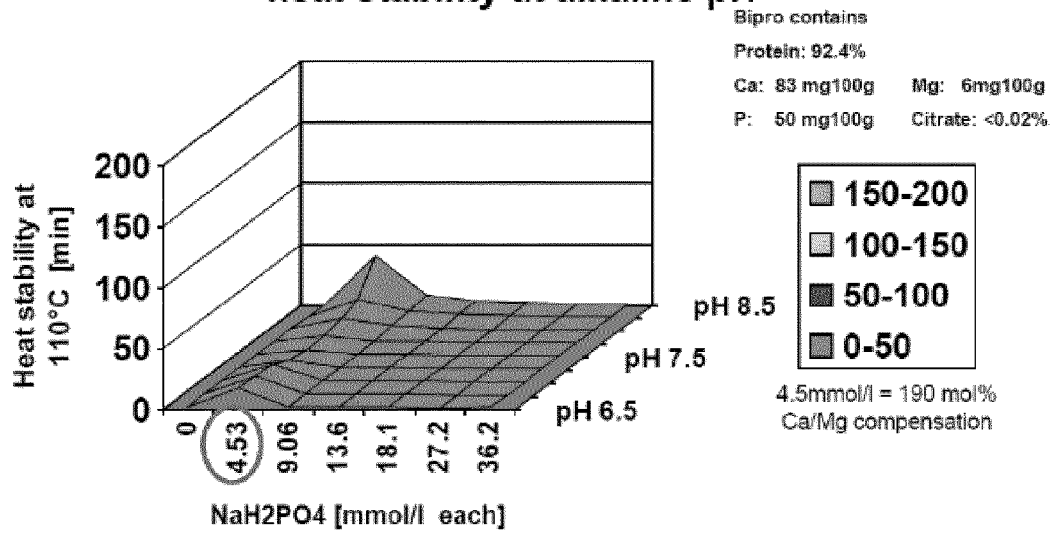

FIG. 7: Show for the inventive composition as described herein that when the and 8 at least one component is phosphate in 0.06% by weight of the heat sterilized composition (based on example 2), less pronounced efficiency was shown at alkaline pH values, but surprisingly positive stabilizing effects at neutral pH values with whey protein isolate (see also example 5 for protocol).

Figure 9:
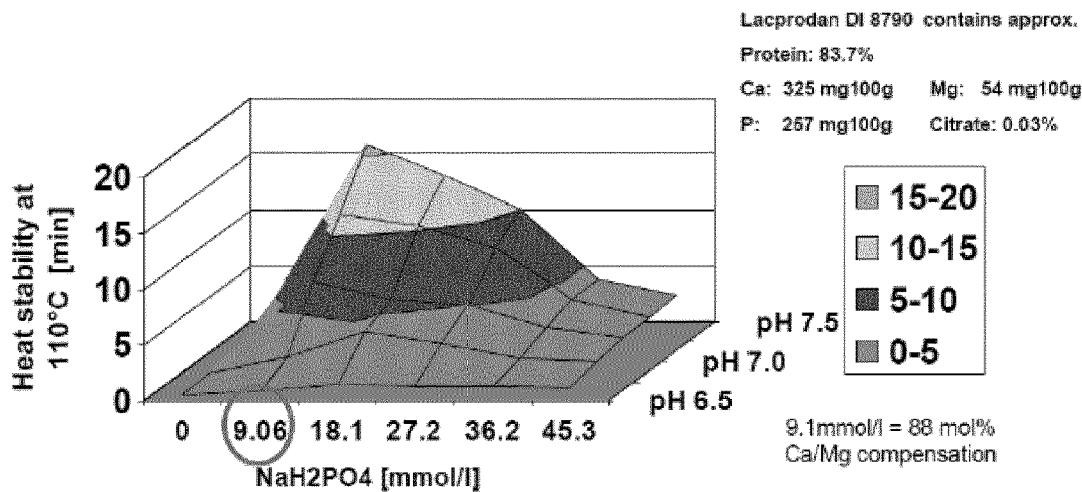

FIG. 9: Shows for the inventive composition as described herein that when the at least one component is phosphate in 0.125% by weight of the heat sterilized composition (based on example 2), less pronounced efficiency was shown at alkaline pH values, but a strong increase in heat stability at neutral pH values with whey protein isolate (see also example 5 for protocol).

Figure 10:
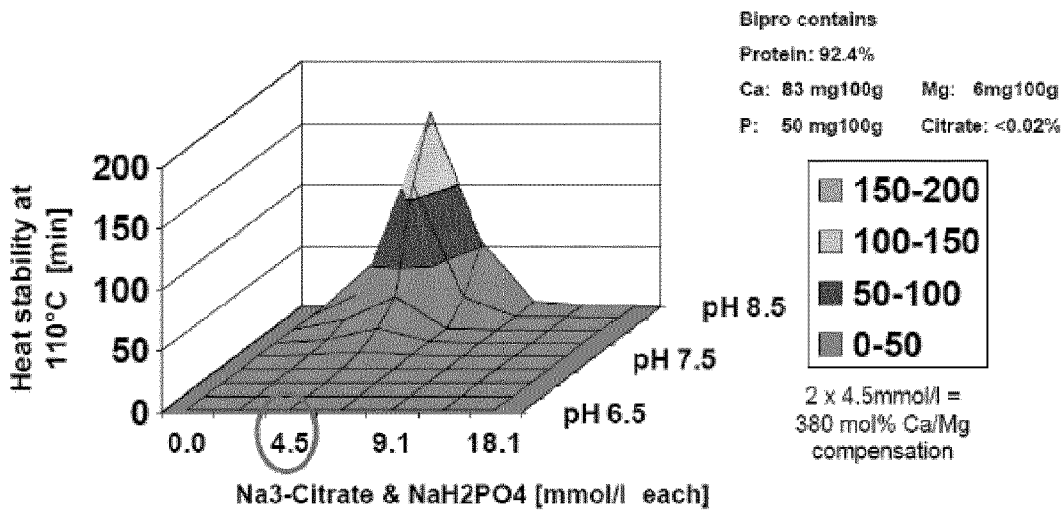

FIG. 10: Shows for the inventive composition as described herein that when the at least one component is phosphate and citrate in 0.06% and 0.13% by weight of the heat sterilized composition respectively (based on example 3), a particularly strong stabilizing effect was seen, particularly at slightly alkaline pH with whey protein isolate (see also example 5 for protocol).

FIG. 11: Shows for the inventive composition as described herein that when the at least one component is phosphate and citrate in 0.26% and 0.125% by weight of the heat sterilized composition respectively (based on example 3), a particularly strong stabilizing effect was seen at slightly alkaline pH with whey protein concentrate (see example 5 for protocol).

FIG. 12: Shows for the inventive composition as described herein that when the at least one component is a saccharide, such as sucrose in for instance 1% by weight of the heat sterilized composition (based on example 4), a particularly strong stabilizing effect was seen at pH 7.5 with whey protein isolate (see example 5 for protocol). More specifically, with 1% sucrose (saccharose) the heat stability increases from about 2 minutes to about 100 minutes.

Figure 13:
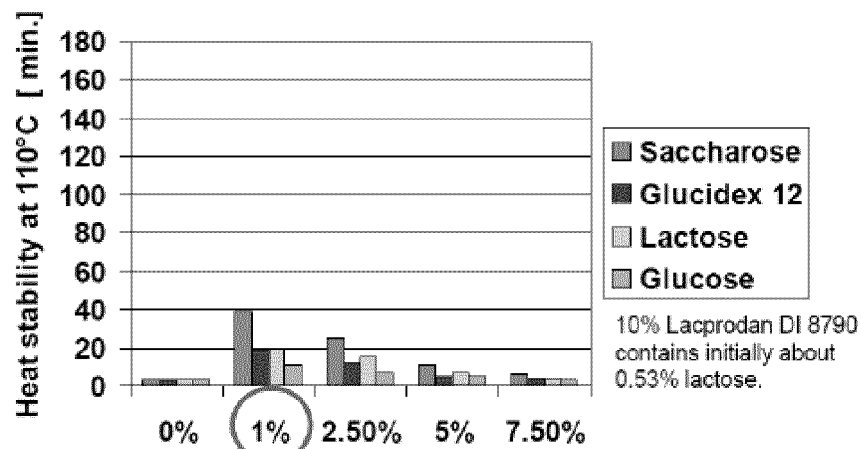

FIG. 13: Shows for the inventive composition as described herein that when the at least one component is a saccharide, such as sucrose in for instance 1% by weight of the heat sterilized composition (based on example 4 for protocol), a particularly strong stabilizing effect was seen at pH 7.5 also with whey protein isolate (see also example 5 for protocol). More specifically, with the addition of 1% sucrose (saccharose) the heat stability increases from 2 minutes to 40 minutes.

EXAMPLES

The following examples are intended to illustrate the invention further. They are not intended to limit the subject matter of the invention thereto.

Example 1

Exemplary Process for Preparing a Heat Sterilized Composition from a Protein Source Comprising Whey Protein—with Citrate Addition To a whey protein source containing:

| Ingredient | % by weight |
|---|---|
| Water | 90 |
| Dry matter | 10 |
| Lacprodan DI 8790 (demineralised Whey Protein concentrate) | 10 | was added 0.26% by weight of the composition $Na_3$-citrate (2.6 g $Na_3$-citrate.$2H_2O$ per litre) which was mixed at 25° C., followed by pH adjustment to a pH of 7.2 with NaOH (1 mol/L)

Said mixture was then UHT treated at 148° C. for 5 seconds, providing a heat sterilised composition comprising a protein source in 8 to 20% by weight based on the weight of the heat sterilized composition.

The obtained liquid composition was without any taste/bitterness. Furthermore this had a viscosity of below 600 mPa·s at 20° C./100 $s^{-1}$ determined using a rotational viscosity meter using a cone/plate geometry.

Furthermore, stability tests were carried out on a test sample (see example 5) under sterilisation conditions as shown in FIG. 5 at a pH of 8.5, showing excellent heat stability.

Example 2

Exemplary Process for Preparing a Heat Sterilized Composition from a Protein Source Comprising Whey Protein—with Phosphate Addition To a whey protein source containing:

| Ingredient | % by weight |
|---|---|
| Water | 90 |
| Dry matter | 10 |
| BiPro Whey Protein isolate | 10 | was added $NaH_2PO_4$ in 0.06% by weight of the composition (0.6 g $NaH_2PO_4$. $H_2O$ per litre) which was mixed at 25° C., followed by pH adjustment to a pH of 7.5 with NaOH (1 mol/L)

Said mixture was then UHT treated at 148° C. for 5 seconds, providing a heat sterilised composition comprising a protein source in 8 to 20% by weight based on the weight of the composition.

The obtained liquid composition was without any taste/bitterness. Furthermore this had a viscosity of below 600 mPa·s at 20° C./100 $s^{-1}$ determined using a rotational viscosity meter using a cone/plate geometry.

Figure 8:
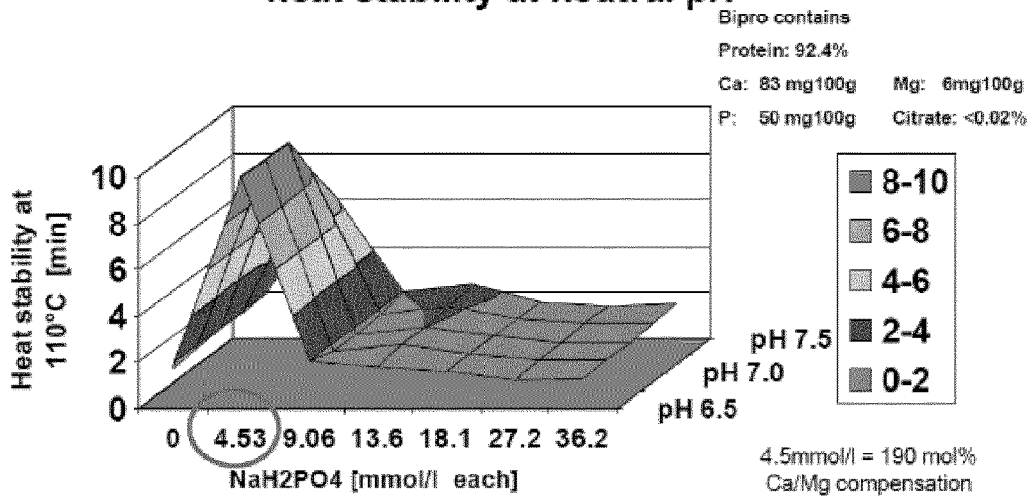

Furthermore, stability tests were carried out on a test sample (see example 5) under sterilisation conditions as shown in FIG. 8 at neutral pH, showing excellent heat stability.

Example 3

Exemplary Process for Preparing a Heat Sterilized Composition from a Protein Source Comprising Whey Protein—with Citrate and Phosphate Addition To a whey protein source containing:

| Ingredient | % by weight |
|---|---|
| Water | 90 |
| Dry matter | 10 |
| BiPro Whey Protein isolate | 10 | was added $NaH_2PO_4$ in 0.06% by weight of the composition (0.6 g $NaH_2PO_4$. $H_2O$ per litre) and 0.13% by weight of the composition $Na_3$-citrate (1.3 g $Na_3$-citrate.$2H_2O$ per litre) which was mixed at 25° C., followed by pH adjustment to a pH of 7.2 with NaOH (1 mol/L)

Said mixture was then UHT treated at 148° C. for 5 seconds, providing a heat sterilised composition comprising a protein source in 8 to 20% by weight based on the weight of the composition.

The obtained liquid composition was without any taste/bitterness. Furthermore this had a viscosity of below 600 mPa·s at 20° C./100 $s^{-1}$ determined using a rotational viscosity meter using a cone/plate geometry.

Furthermore, stability tests were carried out on a test sample (see example 5) under sterilisation conditions as shown in FIG. 10 at pH 8.5, showing excellent heat stability.

Example 4

Exemplary Process for Preparing a Heat Sterilized Composition from a Protein Source Comprising Whey Protein—with Saccharide Addition To a whey protein source containing:

| Ingredient | % by weight |
|---|---|
| Water | 90 |
| Dry matter | 10 |
| BiPro Whey Protein isolate | 10 | was added 1% sucrose by weight of the composition which was mixed at 25° C., followed by pH adjustment to a pH of 7.5 with NaOH (1 mol/L)

Said mixture was then UHT treated at 148° C. for 5 seconds, providing a heat sterilised composition comprising a protein source in 8 to 20% by weight based on the weight of the composition.

The obtained liquid composition was without any taste/bitterness. Furthermore this had a viscosity of below 600 mPa·s at 20° C./100 $s^{-1}$ determined using a rotational viscosity meter using a cone/plate geometry.

Furthermore, stability tests were carried out on a test sample (see example 5) under sterilisation conditions as shown in FIG. 12 at pH 7.5, showing excellent heat stability.

Example 5

Heat Stability Tests

The Heat stability tests performed on the samples prepared in examples 1 to 4 and as further presented in FIGS. 5 to 13 were carried out as follows:

A test sample was prepared by mixing at 25° C. the protein source comprising whey protein with at least one component selected from saccharide and/or phosphate and/or citrate addition following the protocol laid down in examples 1 to 4—but without the heat sterilisation step.

1 ml of the test liquid sample was transferred into a glass test tube (~5 ml volume), which was then installed in a test tube holder positioned in a swinging mechanical system in a temperature controlled oil bath (110° C.), such that heat sterilisation of the liquid test sample may occur.

After immersion of the test tube, the time measurement was started for heat stability determination. The time needed to visually observe the change from a free flowing sample to coagulation (flocculation or gel formation) of the sample was taken as an analytical parameter (indicated in minutes).

The invention claimed is:

1. A process for preparing a heat sterilized composition comprising a protein source in an amount of 1 to 20% by weight based on the weight of the composition, the protein source being whey protein, the process comprising:
    a) heating at a sterilisation temperature at a pH of 5.5 to 9.5 an aqueous solution of the whey protein source and at least one component selected from the group consisting of:
        i) a saccharide component in an amount of 0.5% to 7.5% by weight of the composition;
        ii) a phosphate component in an amount of 0.03% to 3% by weight of the composition; and
        iii) a citrate component in an amount of 2% to 5% by weight of the composition.

2. The process according to claim 1, wherein the heating of the aqueous solution at the sterilization temperature forms the heat sterilized composition comprising the protein source in an amount of 1% to 20% by weight of the composition, in liquid form.

3. The process according to claim 2, further comprising drying the heat sterilized aqueous solution to form a powder of the heat sterilized composition comprising the protein source in an amount of 1% to 20% by weight of the composition.

4. The process according to claim 1, wherein the citrate component is 2% to 3% by weight of the composition.

* * * * *